(12) United States Patent
Dagle et al.

(10) Patent No.: US 10,647,622 B1
(45) Date of Patent: May 12, 2020

(54) SINGLE-REACTOR CONVERSION OF ETHANOL TO 1-/2-BUTENES

(71) Applicant: BATTELLE MEMORIAL INSTITUTE, Richland, WA (US)

(72) Inventors: Robert A. Dagle, Richland, WA (US); Vanessa M. Dagle, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 15/994,531

(22) Filed: May 31, 2018

(51) Int. Cl.
*C07C 1/20* (2006.01)
*C07C 11/08* (2006.01)
*B01J 21/06* (2006.01)
*B01J 35/10* (2006.01)
*B01J 29/035* (2006.01)

(52) U.S. Cl.
CPC ............ *C07C 1/20* (2013.01); *B01J 21/066* (2013.01); *B01J 29/035* (2013.01); *B01J 35/1019* (2013.01); *C07C 11/08* (2013.01); *C07C 2521/06* (2013.01); *C07C 2529/03* (2013.01)

(58) Field of Classification Search
None
See application file for complete search history.

(56) References Cited

U.S. PATENT DOCUMENTS

2016/0082417 A1* 3/2016 Lewandowski ........... C07C 1/20 585/607
2018/0208522 A1* 7/2018 Cadran ..................... B01J 37/06

OTHER PUBLICATIONS

Jones et al. "Investigations into the conversion of ethanol into 1,3-butadiene", Catal. Sci. Technol., 2011, 1, 267-272. (Year: 2011).*
Supporting Information for Jones et al. "Investigations into the conversion of ethanol into 1,3-butadiene", Catal. Sci. Technol., 2011, 1, 267-272. (Year: 2011).*
Sushkevich et al., "Design of a Metal-Promoted Oxide Catalyst for the Selective Synthesis of Butadiene from Ethanol", ChemSusChem 2014, 7, 2527-2536 (Year: 2014).*
Sun et al., "Catalysis Chemistry of Dimethyl Ether Synthesis", ACS Catal. 2014, 4, 3346-3356. (Year: 2014).*

* cited by examiner

*Primary Examiner* — Ali Z Fadhel
(74) *Attorney, Agent, or Firm* — Derek H. Maughan

(57) ABSTRACT

A simplified processes for producing desired chemicals such as butenes from feedstock mixtures containing ethanol. In one set of embodiments this is performed in a single step, wherein a feed containing ethanol in a gas phase is passed over an acidic metal oxide catalyst having a transition metal dispersion of at least 5% on a metal oxide support. The ethanol content of the feedstock mixture may vary from 10 to 100 percent of the feed and in those non-eat applications the ethanol feed may contain water.

2 Claims, 2 Drawing Sheets

SINGLE-REACTOR CONVERSION OF ETHANOL TO 1-/2-BUTENES

STATEMENT AS TO RIGHTS TO DISCLOSURES MADE UNDER FEDERALLY-SPONSORED RESEARCH AND DEVELOPMENT

This disclosure was made with Government support under Contract DE-AC0576RL01830 awarded by the U.S. Department of Energy. The Government has certain rights in the invention.

BACKGROUND OF THE DISCLOSURE

Petroleum depletion and environmental issues caused by the chemical and petrochemical industries have led to a renewal of interest for using biomass as a carbon source for biofuels production. Various research organizations including program offices within the United States Department of Energy have sought, and continue to seek, transformative and revolutionary sustainable bioenergy technologies. Ethanol conversion to biofuels is one of these attractive bioenergy technologies. Ethanol can be commercially produced at large scale from renewable biomass or waste sources, and continuing advancements in production efficiency and feedstock diversification are envisioned to lead to excess ethanol at competitive prices. The broad availability and cost effective supply of ethanol as a feed stock would enable the production of a wide range of fuels and commodity chemicals.

While ethanol supplies are predicted to rise, a reduction in supplies of other commodity chemicals is also expected. A variety of approaches have been taken attempting to identify simple and cost effective processes for generating desired fuels and commodity chemicals in newer, greener and more cost efficient ways. While a variety of processes have been shown to have some efficacy continued development is needed to find methods that can simply and cost effectively produce the desired result and do so in a sufficiently cost effective manner so as to be adopted in industrial and commercial applications. The present disclosure describes significant advances in this regard.

The following description provides examples and information surrounding successful demonstration of a proof of concept for single step conversion of (aqueous) ethanol into butenes, such as 1-butene. As will be explained below in further detail, oligomerization of mixed 1- and 2-butenes, produced by the single step methods described hereafter allow for the creation of various hydrocarbon fuel configurations both in the presence of and/or absence of hydrogen and/or ethylene.

By directly producing a C4-rich olefin mixture (that can then be selectively oligomerized into gasoline, jet and/or diesel fuels) from an ethanol containing steam various advantages are presented including, but not limited to, significant cost reduction in capital expenses and operational expenses as this simplified process allows for a closer term transformation of a feedstock to a useable product. In some embodiments the conversion of ethanol to butenes can be conducted one single reactor. In one arrangement, the present process was demonstrated using an aqueous ethanol feedstock indicating that typical ethanol/water separations may not always be necessary. This coupled with a reduction of stages in additional chemical processing and allows for various simplified operation units, which can present a significant step forward in reducing costs and complexities and moving renewable transportation fuels forward toward a practical reality.

Additional advantages and novel features of the present disclosure will be set forth as follows and will be readily apparent from the descriptions and demonstrations set forth herein. Accordingly, the following descriptions of the present disclosure should be seen as illustrative of the disclosure and not as limiting in any way.

SUMMARY

The present disclosure provides examples of simplified processes for producing desired chemicals such as butenes from feedstocks containing ethanol. In one set of embodiments this is performed in a single step, wherein a feed containing ethanol in a gas phase is passed over an acidic metal oxide catalyst having a transition metal dispersion of at least 5% on a metal oxide support. In some applications the acidic metal oxide catalyst comprises a Group 11 metal. In some instances this Group 11 metal is selected from the group consisting of copper (Cu), silver (Ag), and gold (Au). In one set of embodiments this metal oxide catalyst comprises a silica metal oxide having a surface area of at least 200 m^2/g. The silica metal oxide support comprises a silica metal oxide selected from the group consisting of a high purity silica gel, mesoporous silica and fumed silica. In some instances the silica metal oxide is a high purity SBA16. In other instances high purity SBA15, or Davisil grade 646 may be used. Under some processing conditions hydrogen may be added to the mixture, and ethanol content of the mixture may vary from 10 to 100 percent of the feed. In those non neat applications the ethanol feed may contain water.

In one specific instance a process for producing butene from an ethanol containing feed stream in a single step is described wherein a feed containing ethanol in a gas phase is passed over a Ag/ZrO2/SiO2 catalyst having a transition metal dispersion of at least 30% on a silica metal oxide support to produce butene. In this particular instance the catalyst was 1% Ag/4% ZrO2/SiO2-SBA-16, the temperature was 325° C., the pressure was 1 atm, and a the flow rate was 0.23 hr-1. This process was effective with various mixtures containing various constituent proportions of ethanol and water.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the disclosure of the application, which is measured by the claims, nor is it intended to be limiting as to the scope of the disclosure in any way.

DETAILED DESCRIPTION OF THE DISCLOSURE

The following description includes examples of exemplary modes of implementation. It will be clear from this description of the disclosure that the invention is not limited to these illustrated embodiments but that the disclosure also includes a variety of modifications and embodiments thereto. Therefore, the present description should be seen as illustrative and not limiting. While the disclosure is susceptible of various modifications and alternative constructions, it should be understood, that there is no intention to limit the disclosure to the specific form disclosed, but, on the contrary, the disclosure is to cover all modifications, alternative constructions, and equivalents falling within the spirit and scope of the disclosure as defined in the claims.

The present disclosure includes a series of examples for a converting ethanol in a gas feed into a preselected commodity chemical. In one embodiment this is performed by the single step conversion of ethanol (either aqueous or neat) to 1- and 2-butenes, which can be oligomerized into a variety of materials including gasoline, jet, and diesel fuels and/or into valuable fuel additives and lubricants. This provides a significant advantage over the prior art inasmuch as production of 1- and 2-butene from ethanol is typically performed by first dehydrating ethanol into ethylene and then dimerizing ethylene into 1- and 2-butene in a second step. However as described hereafter, methods for producing 1- and 2-butene mixtures directly from ethanol (in some cases included in a water and ethanol mixture) have been developed that remove this step and make the use of ethanol as a fuel base more practical and economical.

The process uses specially tailored polyfunctional catalysts having a metal component with relatively weak hydrogenation ability (e.g., Ag) and mildly acidic support materials (e.g., ZrO2 supported on SiO2). These catalysts allow for carbon to oxygen and carbon to carbon coupling take place without saturation of the material with hydrogen. This is believed to be obtained by taking advantage of the various oxidation states of a metal (such as silver) and the Lewis Acid site (i.e., acidity) nature of the catalysts. Under certain process conditions, as shown in the attached tables and figures, direct formation of butenes from an ethanol stream in a gaseous phase, without the need for additional process steps as required by the prior art embodiments.

Figure 1:
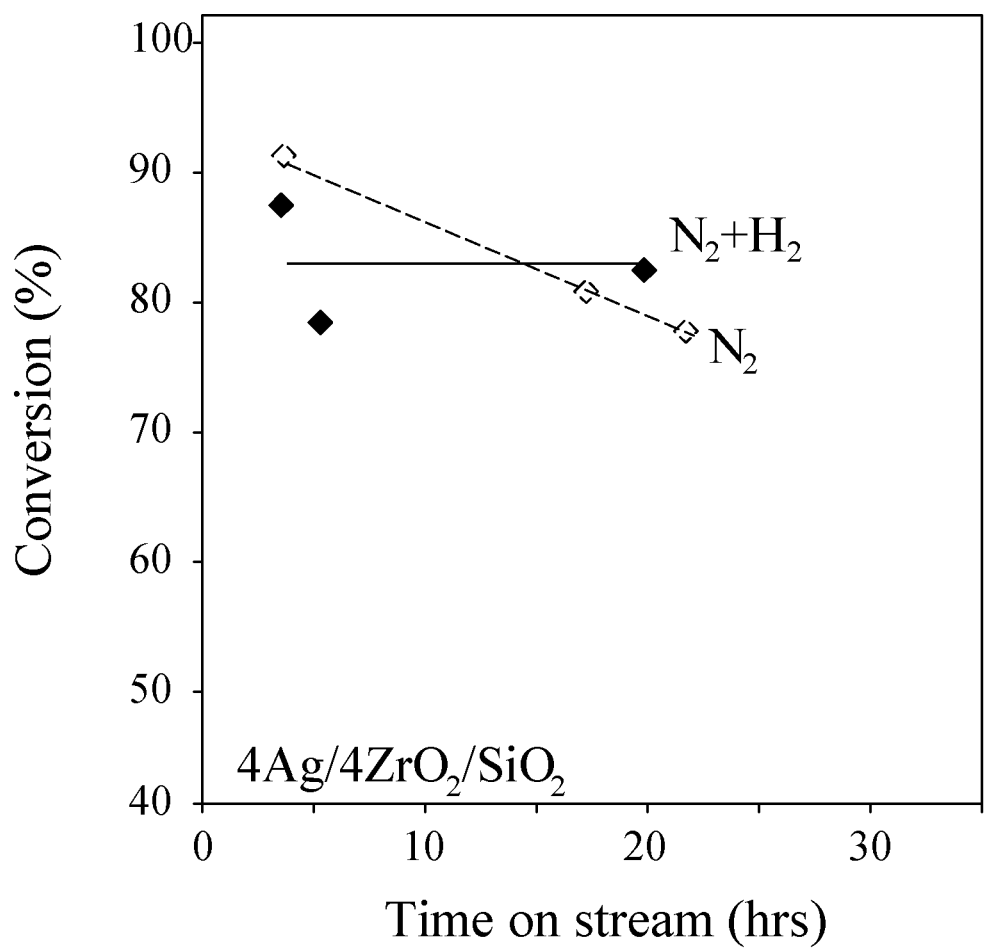
FIG. 1 shows ethanol conversion as a function of time in a first embodiment of the invention.
Figure 2:
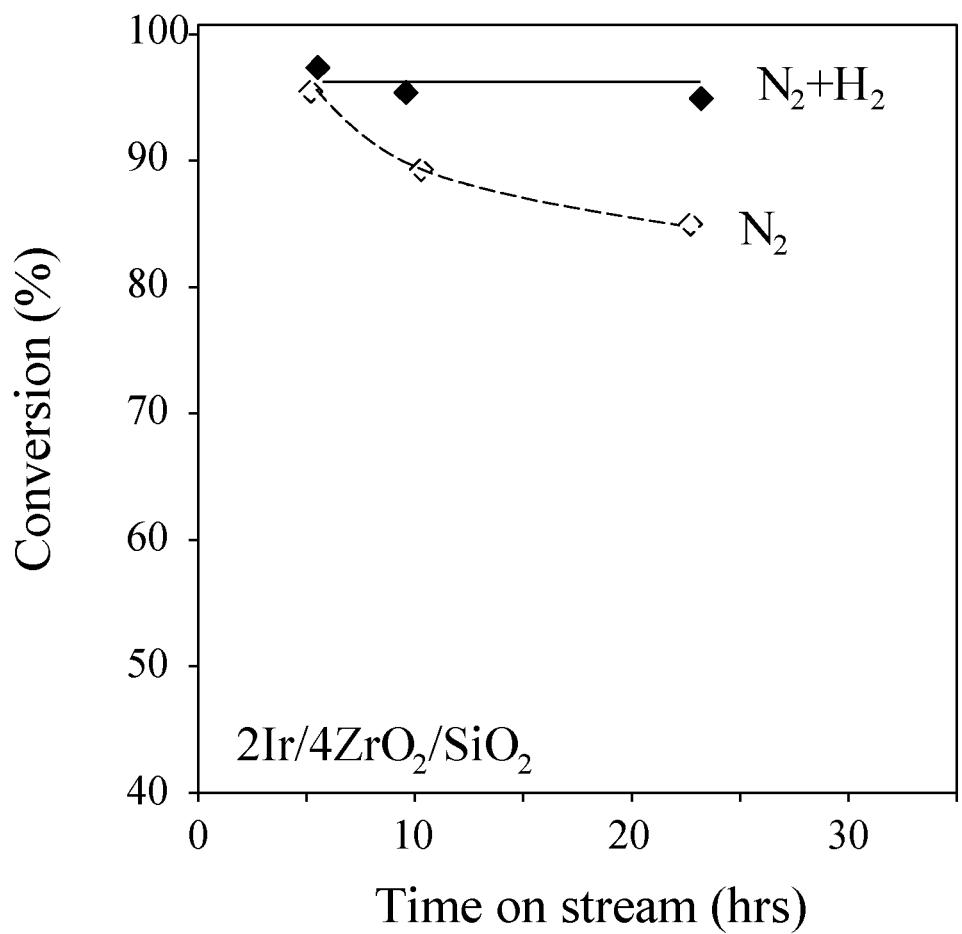
FIG. 2 shows ethanol conversion as a function of time in a second embodiment of the invention.

Examples of such instantiations are provided in FIGS. 1 and 2 wherein the time on stream in hours and the conversion percentages are shown for particular embodiments where in a 24.3% ethanol feed in a N2 or N2 and H2 mixture is shown passing over a 4Ag/4ZrO2/SiO2 (Davisil 646) catalyst (FIG. 1) or a 2Ir/4ZrO2/SiO2 catalyst under the following conditions. Temperature 325 degrees C., Pressure 1 atm, WHSV 0.23/hr. As these figures show conversion percentages are relatively high (>75 percent) over a designated period of time. While these exemplary samples are provided it is to be distinctly understood that the invention are not limited to these examples but may be variously alternatively embodied as necessary.

In one application a 24% ethanol feed in a gaseous state was passed over a 4Ag/4ZrO2/SiO2/SBA16 catalyst under the following conditions: temperature 325° C., pressure=7 bar (100 psig), flow rate (space velocity) WHSV=0.23 hr-1. An incremental addition of $H_2$ to the feed gas from 0% to 100% (carrier gas content) was varied and produced the results shown in Table 1. Various other modifications to the processing conditions effectuated the variations described and set forth in subsequent tables that follow thereafter.

TABLE 1

Effect of Hydrogen on process results

| H2% | 0% H2 | 18.5% H2 | 45% H2 | 100% H2 |
|---|---|---|---|---|
| Carbon Balance | 91.0 | 89.0 | 96.3 | 97.5 |
| Conversion % | 99 | 98 | 95.9 | 85.2 |
| C2 = | 8.6 | 6.2 | 9.6 | 25.8 |
| C3 = | 0.0 | 2.0 | 2.5 | 3.2 |
| C4 = | 15.8 | 35.3 | 41.7 | 51.1 |
| C5 = | 0.9 | 1.8 | 1.5 | 0.7 |
| BD butadiene | 63.7 | 6.6 | 1.2 | 0.4 |
| C2-C6 alkanes | 0.5 | 1.3 | 2.0 | 2.8 |
| Acetaldehyde HAC | 2.9 | 0.7 | 0.8 | 2.3 |
| Other Oxygenates (e.g.C1-C4 alcohols, Ethyl acetate, acetic acid, 2-butanone, acetone) | 3.8 | 7.5 | 10.2 | 5.3 |
| Crotonaldehyde | 0.7 | 0 | 0 | 0 |
| Diethylether | 3.1 | 4.1 | 4.0 | 8.4 |
| C4-C8 olefins Liquid | 0 | 10.0 | 11.9 | 0 |
| Cyclic Hydrocarbon Liquids | 0 | 24.5 | 14.6 | 0 |
| Olefins w/o Butadiene Total Gas and Liquid | 25.3 | 55.3 | 67.2 | 80.8 |
| Olefins w/o Butadiene Total in gas | 25.3 | 45.3 | 55.3 | 80.8 |

As the data in this table shows, as the percentage of hydrogen increases the percentage of the ethanol converted decreases from 99 to 85% accompanied by an increase of the 1- and 2-butene combined selectivity from ~16 to 51%. Meanwhile the ethylene selectivity increased from ~8.6 to 26% while the butadiene selectivity decreased from 63.7% to 0%. Generally speaking, 1- and 2-butene is formed at the expense of 1,3-butadiene when $H_2$ content is added to the feed. Table 2 shows the effect of altering the flow rate (space velocity) on catalytic performance for the conversion of ethanol to butenes over this same catalytic composition.

TABLE 2

Effect of flow rate (space velocity) variation on catalytic performance

| Run ID | 227 | 243 | 272 | 237 | 253 | 231 | 233 | 235 |
|---|---|---|---|---|---|---|---|---|
| Pressure (Psig) | 100 | 100 | 100 | 100 | 100 | 100 | 100 | 100 |
| WHSV (hr−1) | 0.10 | 0.23 | 0.7 | 1.4 | 2.0 | 3.6 | 7.3 | 14.6 |
| Conversion (%) | 87.6 | 87.1 | 75.3 | 67.5 | 65.7 | 65.5 | 34.9 | 11.7 |

TABLE 2-continued

Effect of flow rate (space velocity) variation on catalytic performance

| Run ID | | 227 | 243 | 272 | 237 | 253 | 231 | 233 | 235 |
|---|---|---|---|---|---|---|---|---|---|
| Carbon Balance | | 85 | 104 | 104 | 112 | 95.5 | 91 | 103 | 104 |
| Selectivity % | butadiene | 0.0 | 3.8 | 4.2 | 19.5 | 0.6 | 0 | 0 | 0 |
| | C2= | 7.1 | 16.7 | 2.9 | 13.1 | 10.6 | 9.0 | 11.1 | 15.0 |
| | C3= | 1.0 | 2.7 | 1.2 | 1.5 | 1.7 | 1.2 | 0.9 | 0.8 |
| | C4= | 47.3 | 40.7 | 46.3 | 24.3 | 51.1 | 51.9 | 27.9 | 13.0 |
| | C5= | 0.2 | 0.6 | 1.0 | 0.3 | 0.2 | 0.5 | 0.3 | 0.0 |
| | Diethylether | 10.2 | 8.6 | 3.3 | 6.8 | 6.2 | 6.5 | 6.5 | 7.7 |
| | Acetaldehyde | 0.6 | 1.4 | 3.1 | 3.7 | 7.2 | 8.1 | 18.6 | 26.5 |
| | C2-C5 Alkanes | 14.6 | 1.6 | 0.8 | 1.0 | 2.5 | 1.7 | 1.0 | 0.9 |
| | C4+ Alkanes Liquids | 6.9 | 0 | 0 | 0 | 0 | 0 | 0 | 0 |
| | Butyraldeheyde | 0 | 1.9 | 2.1 | 15.5 | 16.2 | 17 | 26.1 | 31.4 |
| | C4-C8 olefins liquids | 4.2 | 11.0 | 16.1 | 0 | 0 | 0 | 0 | 0 |
| | butanol | 0 | 0.1 | 1.2 | 0.2 | 1.7 | 1.7 | 1.8 | 1.2 |
| | Others (e.g. cyclic hydrocarbons and oxygenates (e.g. C1-C4 alcohols, ethyl acetate, acetic acid, 2-butanone, acetone) | 15.0 | 10.9 | 17.8 | 14.1 | 2.0 | 2.4 | 6.8 | 3.5 |
| | Total olefins | 59.8 | 71.7 | 67.5 | 39.2 | 63.6 | 62.6 | 40.2 | 28.8 |

Table 3 shows the effect of pressure on catalytic performance for the conversion of ethanol to butenes on a 4Ag/4ZrO2/SiO2/SBA16 catalyst under the following conditions: temperature 325° C., pressure=7 bar (100 psig), 24% ethanol in hydrogen gas, time on stream (TOS) 5 hours.

TABLE 3

| Run ID | | MO236 | MO237 | MO216 |
|---|---|---|---|---|
| Pressure (Psig) | | atm | 100 | 200 |
| WHSV (hr-1) | | 1.4 | 1.4 | 1.4 |
| Conversion % | | 53.4 | 67.5 | 82.5 |
| Carbon Balance | | 110 | 112 | 106 |
| Selectivity % | butadiene | 43.8 | 19.5 | 0 |
| | C2 = | 22.2 | 13.1 | 7.1 |
| | C3 = | 1.2 | 1.5 | 0 |
| | C4 = | 8.2 | 24.3 | 28.2 |
| | diethylether | 11.3 | 6.8 | 8.2 |
| | acetaldehyde | 8.1 | 3.7 | 2.7 |
| | butyraldehyde | 2.1 | 15.5 | 3.8 |
| | BuOH | 0.6 | 0.2 | 2.3 |
| | C2-C5 alkanes | 0.2 | 1.0 | 9.0 |
| | C4-C8 olefins in liquid | 0 | 0 | 16.0 |
| | Others (e.g. cyclic hydrocarbons and oxygenates (C1-C4 alcohols, ethyl acetate, acetic acid, 2-butanone, acetone) | 2.3 | 14.4 | 20.6 |
| | C6-C7 alkanes | 0 | 0 | 2.1 |
| | Total olefins | 31.6 | 38.9 | 51.3 |

Table 4 shows the effect of water content in the ethanol feed stream on the conversion of ethanol to butenes when passed over a 4Ag/4ZrO2/SiO2/SBA16 catalyst under the following conditions: temperature 325° C., pressure=7 bar (100 psig), 11% ethanol in gas, flow rate (space velocity) WHSV=0.23 hr-1.

TABLE 4

| Feed Composition | | Pure EtOH | 95% EtOH in H2O | 35% EtOH in H2O |
|---|---|---|---|---|
| Pressure (Psig) | | 100 | 100 | 100 |
| WHSV (hr-1) | | 0.23 | 0.23 | 0.23 |
| Conversion % | | 93.9 | 93.9 | 76.4 |
| Carbon Balance | | 120 | 112 | 103 |
| Selectivity % | butadiene | 0 | 0 | 0 |
| | C2 = | 25.7 | 19.4 | 8.8 |
| | C3 = | 2.0 | 1.6 | 2.1 |
| | C4 = | 57.7 | 56.9 | 54.8 |
| | diethylether | 6.0 | 6.1 | 2.8 |
| | acetaldehyde | 0.4 | 0.3 | 6.5 |
| | butyraldehyde | 0.1 | 0.1 | 2.3 |
| | BuOH | 0 | 0 | 2.6 |
| | C2-C5 alkanes | 6.1 | 12.9 | 2.1 |
| | C4-C8 olefins in liquid | 0 | 0 | 0 |
| | Acetic Acid | 0.7 | 0.5 | 11.8 |
| | Others (cyclic hydrocarbons and oxygenates (C1-C4 alcohols, ethyl acetate, acetic acid, 2-butanone, acetone) | 1.3 | 2.2 | 6.2 |
| | Total olefins | 85.4 | 77.9 | 65.7 |

In addition to these results we also demonstrated that catalytic stability is enhanced when $H_2$ is added to $N_2$ as the carrier gas for the process. (See FIGS. 1 and 2) Hence the addition of $H_2$ (to the ethanol feed) not only alters the product distribution favoring a butene product slate but it also significantly suppresses coking allowing for enhanced catalytic stability. While $H_2$ addition to the feed may add cost to the overall process, hydrogen is usually needed anyhow for fuels production as the final olefin product after oligomerization needs to be hydrotreated. Thus, the added hydrogen can be used in the latter hydrotreatment step and unconverted hydrogen can be recycled to the front end of the process.

Higher contact times favor the formation of 1- and 2-butenes. Decreasing the space velocity from 14.6 to 0.23 hr-1 while operating under $H_2$ gas leads to an increase of the conversion from ~11 to 85% and an increase of both 1- and 2-butenes and ethylene selectivity from ~13 to 51% and ~15 to 26%, respectively. In addition the fractions transition to acetaldehyde and butyraldehyde decrease while the effect on butadiene selectivity remains negligible. This suggests that the mechanism for butene formation involves the conversion of acetaldehyde to crotyl alcohol, isomerization of crotyl alcohol to butyraldehyde, and butenes formation from butyraldehyde deoxygenation. The effect of operating pressure was also investigated and it was found that higher pressure favors the formation of butenes at the expense of butadiene (see Table 3).

For example, increasing the pressure from atmospheric to 14 bar while operating under $H_2$ gas leads to an increase of the conversion from 52 to 83% and an increase of the C4+ olefins selectivity from 8.1 to 44% while the selectivity toward butadiene and ethylene decreases from 43 to 0% and 22 to 7%, respectively. Addition of water to the feed also leads to a decrease of the conversion, from 94.0%, with 100% ethanol as a feedstock, and to 76%, with 35% ethanol in $H_2O$ as a feedstock (see Table 4). The butenes selectivity is only slightly affected by the presence of water since it decreases from 58% to 55%. However, this demonstrates that diluted feeds of ethanol can be used as feedstock and separation of water and ethanol is not required prior to conversion. In addition alteration and modification of a variety of other factors including $H_2$ concentration, $H_2O$ concentration, space velocity and pressure were demonstrated to have significant effect on conversion, selectivity, and stability. $H_2$-addition to the feed favors the formation of 1- and 2-butene at the expense of butadiene.

The product from the ethanol conversion contains primarily butenes and ethylene olefins mixed with $H_2$ which can be oligmerized for the formation of fuels. In a series of experiments intended to demonstrate the feasibility of producing fuels from the olefin precursors obtained from the single step process we co-feed ethylene and/or $H_2$ with butene mixtures over zeolite catalysts and obtained favorable results. Table 5 shows the results of this testing under the following conditions. Zeolite beta catalyst, temperature 260 degrees C.; pressure 200 psig; WHSV 0.42-46 hr-1. Time on stream extended up to 50 hours These results show that oligomerization of butenes in the presence of $H_2$ was feasible. Adding $H_2$ to the feed leads to about 20% lower C8+olefins production. Adding ethylene to the feed was also demonstrated to lead to higher paraffins/olefins ratio due to hydrogenation activity but does not affect the production of C8+olefins since the same quantity of product was obtained w and w/o ethylene addition to the feed. The ratio paraffins/olefins is equal to about 0.4 in the presence of H2+ethylene as opposed to <0.5 without H2+ethylene indicating a significant hydrogenation activity. The quantity of C8 olefins produced is about 10% higher in the presence of H2 and ethylene and is likely due to ethylene oligomerization to C8+product occurring in the meantime as butenes oligomerization. Thus, we demonstrate that oligomerization of 1-butene is feasible in the presence of $H_2$ and/or ethylene co-feed.

The product distribution for 2-butene oligomerization to be very similar to that of 1-butene. Thus, a feed containing mixtures and 1- and 2-butene arising from the single step process would produce a similar product distribution when passed through this oligmerization step. This process provides a promising way for developing a bio-derived jet/diesel fuel from ethanol upon oligomerization followed by hydrogenation as demonstrated by this disclosure.

In another set of experiments various catalyst configurations were tested to determine the effect of various catalyst compositions and performance parameters on obtaining the desired outcomes. The following Table 6 presents the data from this testing. This data demonstrates that monitoring the quantity and quality of metals in the catalyst composition is important in maintaining desired performance. Experimental results have shown that when Ag percentages rise above that 16 percent that saturation of the hydrocarbon increases and increased yields of C2-C5 alkanes begin to take place. We believe that this is due to the ability of Ag to become partially oxidized which may be a factor in hydrogenation suppression. Similarly, adding other metals with stronger hydrogenation capability such as Ir, Pd, or Pt will render a significant number of parrafins. These metals that are stronger for hydrogenation will also push toward the formation of alkanes rather than the desired alkenes. This was demonstrated even 0.4% Ir was added to the 4Ag/4Zr/$SiO_2$ system."

TABLE 5

| Feed | Olefin Liquid Products (mg/min/gram catalyst) | | | | | | | | | | | |
| --- | --- | --- | --- | --- | --- | --- | --- | --- | --- | --- | --- | --- |
| | C4 | C5 | C6 | C7 | C8 | C9 | C10 | C11 | C12 | C13 | C14 | C15 |
| 1-butene | 2.2 | 0.0 | 0.6 | 8.7 | 50.0 | 10.3 | 3.3 | 4.0 | 43.4 | 3.9 | 0.7 | 5.2 |
| H2 + 1-butene | 3.0 | 0.4 | 2.3 | 6.6 | 36.2 | 12.9 | 8.7 | 7.6 | 28.0 | 2.4 | 1.5 | 0.5 |
| C2= + 1-butene | 3.8 | 1.3 | 4.1 | 11.2 | 55.8 | 16.5 | 9.0 | 10.3 | 37.2 | 4.6 | 4.2 | 0.0 |
| H2 + C2= + 1butene | 3.8 | 1.4 | 4.6 | 12. | 53.9 | 14.1 | 7.8 | 15.2 | 38.5 | 4.7 | 1.8 | 0.0 |

TABLE 6

Operating Conditions
Pressure 1000 psig, Temp 325 C., 24% EtOH in H2

| Catalyst | WHSV (hr−1) | Conv (%) | C bal | Selectivity (%) | | | | | | | | | | | | Total olefins |
|---|---|---|---|---|---|---|---|---|---|---|---|---|---|---|---|---|
| | | | | B | C2= | C3= | C4= | C5= | D | A | C2-C5 Alkanes | BA | BL | MEK | Others* | |
| 4% Ag/1% ZrO2/SiO2 | 1.4 | 49.7 | 95.2 | 0 | 5.1 | 0.0 | 54.2 | 0.2 | 4.0 | 4.1 | 1.9 | 4.1 | 8.0 | 5.1 | 13.3 | 59.5 |
| 4% Ag/2% ZrO2/SiO2 | 1.4 | 61.5 | 95.8 | 7.8 | 4.5 | 0.0 | 56.6 | 1.2 | 6.5 | 2.8 | 0.6 | 2.8 | 3.5 | 4.7 | 5.2 | 62.4 |
| 4% Ag/4% ZrO2/SiO2 | 1.4 | 67.5 | 112 | 19.5 | 13.1 | 1.5 | 24.3 | 0.3 | 6.8 | 15.5 | 1.0 | 15.5 | 0.2 | 12.2 | 1.9 | 39.2 |
| 1Ag/4% ZrO2/SiO2 | 0.5 | 57.7 | 107 | 39.8 | 5.9 | 2.2 | 28.5 | 0.2 | 8.7 | 0 | 0.4 | 0 | 0.7 | 7.2 | 3.4 | 36.8 |
| 1Ag/4% ZrO2/SiO2 | 1.4 | 33.8 | 107 | 46.6 | 5.2 | 1.5 | 15.2 | 0.4 | 8.5 | 0 | 0.4 | 0 | 1.3 | 12.2 | 3.6 | 22.3 |
| 2Ag/4% ZrO2/SiO2 | 1.4 | 52.6 | 105 | 27.2 | 3.5 | 1.5 | 38.1 | 0.9 | 7.1 | 2.8 | 0.5 | 2.8 | 2.4 | 6.0 | 3.5 | 44.0 |
| 4% Ag/4% ZrO2/SiO2 | 1.4 | 67.5 | 112 | 19.5 | 13.1 | 1.5 | 24.3 | 0.3 | 6.8 | 15.5 | 1.0 | 15.5 | 0.2 | 12.2 | 1.9 | 39.2 |
| 8% Ag/4% ZrO2/SiO2 | 1.4 | 65.2 | 100.6 | 9.4 | 5.6 | 1.7 | 59.8 | 1.1 | 7.0 | 3.1 | 0.7 | 3.1 | 1.5 | 3.8 | 2.0 | 68.2 |
| 0.4Ir4Ag/4ZrO2/SBA16 | 0.23 | 89.1 | 80.8 | 0 | 0.1 | 1.2 | 8.7 | 2.9 | 5.1 | 1.5 | 55.3 | 0 | 0.9 | | 24.3 | 12.9 |
| 4Ag4ZrO2/SBA16 | 0.23 | 87.1 | 103 | 3.8 | 16.7 | 2.7 | 40.7 | 0.6 | 8.6 | 1.4 | 1.6 | 1.9 | 0.1 | | 10.9 | 71.7 |
| 16Ag4ZrO2/SiO2 | 1.4 | 66.3 | 91 | 0 | 8.8 | 1.7 | 57.8 | 1.2 | 6.0 | 3.9 | 3.1 | 3.3 | 3.4 | 3.8 | 7.0 | 69.5 |

B—Butadiene, D—Diethylether, A—acetylaldehyde, C2-C5 Alkanes, BA, Butyrladehyde, BL—butanol, Others: CO2, MeOh, PrOh, PenOH, EA, Acetic Acid, pentanone, phenol/cresol for MO277

While various preferred embodiments of the disclosure are shown and described, it is to be distinctly understood that this disclosure is not limited thereto but may be variously embodied to practice within the scope of the following claims. From the foregoing description, it will be apparent that various changes may be made without departing from the spirit and scope of the disclosure as defined by the following claims.

What is claimed is:

1. A process for producing butene from a feed stream containing ethanol in a single step, the method comprising the step of:

passing a feed containing ethanol in a gas phase over a 4 weight % Ag/4 weight % ZrO2/SiO2-SBA-16 catalyst having a Ag transition metal dispersion of at least 30% at a temperature of 325° C., pressure of 7 bar and a flow rate of 0.23 hr-1 in the presence of a hydrogen carrier to directly form butenes with selectivity of greater than 15.8% from ethanol whereby the relatively weak hydrogenation ability of the Ag and mildly acidic support materials provide a preference for carbon to oxygen and carbon to carbon coupling to take place without hydrogen saturation.

2. The process of claim 1 wherein the feed contains water.

* * * * *